(12) United States Patent
Nidam

(10) Patent No.: US 11,193,679 B2
(45) Date of Patent: Dec. 7, 2021

(54) TECHNIQUE FOR DENATURING OF SMALL ORGANIC ITEMS IN PREMISES

(71) Applicant: DUSMIT LTD, Kfar Hanagid (IL)

(72) Inventor: Ofer Nidam, Kfar Hanagid (IL)

(73) Assignee: DUSMIT LTD, Kfar Hanagid (IL)

( * ) Notice: Subject to any disclaimer, the term of this patent is extended or adjusted under 35 U.S.C. 154(b) by 0 days.

(21) Appl. No.: 16/973,923

(22) PCT Filed: Jun. 6, 2019

(86) PCT No.: PCT/IL2019/050648
§ 371 (c)(1),
(2) Date: Dec. 10, 2020

(87) PCT Pub. No.: WO2019/239406
PCT Pub. Date: Dec. 19, 2019

(65) Prior Publication Data
US 2021/0247080 A1  Aug. 12, 2021

(30) Foreign Application Priority Data

Jun. 11, 2018  (IL) .......................................... 259945

(51) Int. Cl.
| | |
|---|---|
| *F24F 3/16* | (2021.01) |
| *A61L 9/16* | (2006.01) |
| *F24F 7/08* | (2006.01) |
| *F24F 13/22* | (2006.01) |
| *F24F 13/24* | (2006.01) |

(52) U.S. Cl.
CPC ............... *F24F 3/16* (2013.01); *A61L 9/16* (2013.01); *F24F 7/08* (2013.01); *F24F 13/222* (2013.01); *F24F 13/24* (2013.01); *A61L 2209/111* (2013.01); *A61L 2209/134* (2013.01); *A61L 2209/16* (2013.01)

(58) Field of Classification Search
CPC ..................................... A61L 9/16; F24F 3/16
See application file for complete search history.

(56) References Cited

U.S. PATENT DOCUMENTS

2020/0061230 A1\* 2/2020 Hammadi ................. A61L 9/16

FOREIGN PATENT DOCUMENTS

| CN | 104174058 A | 12/2014 |
|---|---|---|
| CN | 105546649 A | 5/2016 |

(Continued)

OTHER PUBLICATIONS

CN Office Action in Application No. 201980039546.9 dated Sep. 30, 2021.

*Primary Examiner* — Robert A Hopkins
(74) *Attorney, Agent, or Firm* — Maschoff Brennan

(57) ABSTRACT

A system and a method are proposed for sanitizing air in premises. The system comprises an air compressor for sucking and then compressing the air supposedly comprising noxious and/or allergenic small items up to a denaturing pressure. The system is provided with a controllable pressure tank for denaturing there-inside the mentioned small items supplied with the compressed air. The tank controllably receives the compressed air from the compressor, heats and maintains the compressed air within a denaturing temperature range and discharges the compressed sanitized air to the premises, so that the discharged sanitized air cools down while expanding.

20 Claims, 7 Drawing Sheets

(56) References Cited

FOREIGN PATENT DOCUMENTS

| | | |
|---|---:|---|
| CN | 105664206 A | 6/2016 |
| JP | H07136641 A | 5/1995 |
| JP | H10-128026 A | 5/1998 |
| JP | H10146514 A | 6/1998 |
| SU | 952261 | 8/1982 |
| WO | 9602281 A1 | 2/1996 |
| WO | 2016/085416 A1 | 6/2016 |

\* cited by examiner

TECHNIQUE FOR DENATURING OF SMALL ORGANIC ITEMS IN PREMISES

FIELD OF THE INVENTION

The present invention relates to a method and a system for sanitizing/purifying of air in premises, for example in a room, office, hospital, kinder garden or the like. More specifically, the technique is intended for denaturing or killing small noxious items and organisms such as dust mites, mold, bacteria etc.

BACKGROUND OF THE INVENTION

House dust mites and other noxious small organisms usually develop within the interior of a building. Usually, there is lack of sufficient ventilation and sunlight indoors, and those are conditions for development of bacteria and other small organisms, for example development of mold and mildew due to dampness or development of dust mites in textile, beds and the like. The small organisms and/or products of their life cycle often cause allergic reactions of people who work or live in such environment. Pollen of plants and flowers are also known to cause allergy, especially in spring when concentration of the pollen in air grows so that considerable amounts of the pollen may be brought to the premises from outside.

Lack of ventilation also helps the bacteria and allergens in the air to spread so as a result of all that there are: infection spreading, contagious diseases, respiratory problems, development of asthma, asthma attacks, development of allergy sensitization.

There are solutions for purifying the indoor air, for example, dehumidifiers, HEPA filters based on air filtration devices. Such solutions appear to be insufficient against the mentioned noxious species and items. To those who suffer from such organisms/items, doctors just recommend to ventilate the room, to close the window during spring for pollen sufferers, or to somehow purify air in the premises.

There are other solutions, for example the following devices for neutralizing of small organisms.

WO16085416 A1 discloses an air conditioner that is supposed to kill dust mites, bacteria, and fungus using humidity control. It comprises an air-reconditioning unit installed in the outdoor unit of the air conditioner. The air-reconditioning unit comprises an air pump creating air suction in two attached tubes. A first tube brings in moisture from a water-based heat exchanger. A second tube brings in heat from a fan. The mixture is sent through an air pipe back into a room through the indoor air conditioner unit. The air conditioner controls the level of moisture and heat brought in from outside into the room. At professional forums, some doctors consider such a technology not effective for killing dust mites.

SU952261T describes a device for purification of air, to be used in industry for microbial production of enzymes, which requires a continuous supply of sterile air. A device for bacterial air cleaning comprises a housing with nozzles and an electrical heating tube of sintered porous metal powder. In one known device, air enters into the chamber having heating elements, and then into another chamber with an element of sintered powder metal (stainless steel). To reduce the size of the device while improving the quality of air purification, the device for purifying air comprises a housing and arranged therein a hollow porous electric heating tube of sintered metal powder.

One of the main problems with the denaturing devices is heating of the room while operating, i.e. producing excessive heat without efficiently removing the heat from the device/room.

There is a long felt need in a reliable technique and/or in a compact and simple appliance which would allow effectively and continuously sanitizing air at home, in an office, etc. without excessive heating of the air.

OBJECT AND SUMMARY OF THE INVENTION

It is therefore an object of the present invention to provide an effective technique for continuously sanitizing air in a premises so as to eliminate (denature) small noxious or allergenic organisms and items in the air.

The noxious/allergenic small organisms or items may be understood as one or more from the following non-exhaustive list: bacteria, viruses, germs, mold, mildew, dust mite allergens, cockroaches allergens, other insects, droppings/feces of insects or animals, pollen etc.

Based on the study and experiments conducted by the Inventor, there is provided a method and a system for sanitizing air in a premises.

Briefly, the proposed sanitizing system comprises at least:
an air compressor (for example, a controllable air compressor) for sucking air supposedly comprising noxious and/or allergenic small items, and compressing the sucked air up to a denaturing pressure,
a controllable pressure tank for denaturing there-inside said noxious and/or allergenic small items, said tank being adapted for continuously and controllably:
  introducing the compressed air from the compressor to the tank (for example, via a non-return valve),
  heating the compressed air in the tank and maintaining the compressed air within a denaturing temperature range,
  discharging the compressed sanitized air to the premises (for example, via a controllable valve), wherein the discharged air cools down while expanding.

The system may comprise a first and/or a second heatsink(s) to cool the controllable air compressor, to this end said air compressor (more specifically, the compressor's head) may be respectively provided with a first heat exchanging radiator and/or a second heat exchanging radiator.

For example, the heat exchanging radiators may be in the form of ridges (forming a so-called comb or so-called cooling fins) provided on the compressor housing.

In another example, the heat exchanging radiators may comprise heat connectors or heat pipes (metal portions for transferring heat between the compressor and the heatsink).

In a third example, the heat exchanging radiators may comprise any combination of heat exchanging members: ridges, heat connectors, etc.

Preferably, the air compressor is equipped with both of the heatsinks.

The first heatsink may be an air heatsink configured for cooling the air compressor by air. For example, the first heatsink may comprise the first radiator of the air compressor, placed in a flow of the outgoing cooled air produced by an air conditioner. Such a heat sink may bring the compressor temperature to about 30 degrees Celsius.

The second heatsink may be a water heatsink configured for cooling the air compressor by water. For example, the water heatsink may be in the form of a refillable water reservoir, in which the second radiator of the air compressor is introduced so as to be at least partially submerged in water.

In one embodiment of the system, it may be a stand-alone device which can be placed at any location in the premises.

In an alternative embodiment of the system, it may be accommodated in an internal unit of an air conditioner (A/C). In this case it may be called an integrated device.

In any of the above-mentioned embodiments, the water reservoir of the water heatsink may be refillable with water, for example with condensate of the air conditioner.

Usually, both of the heatsinks (the first one and the second one) are required during warm seasons. In such seasons, the air in the room is quite hot regardless presence of the proposed system (device). Consequently, the air in the room must anyway be cooled, for example, by an air conditioner. If the air conditioner works for cooling, it produces both the cool air and the cool condensate which—as the Inventor suggests—may be used for cooling the compressor of the device.

Another situation takes place during cold seasons, when the temperature in the premises is low and the air in the room requires heating.

The stand-alone device may be still cooled by the room air, thus heating the air.

The integrated device may still be cooled by air outputted from the A/C, thus heating that air and therefore saving energy required for heating the air by the A/C.

The water heatsink may become inactive in the heating mode of the A/C since no condensate is refilled in the reservoir from the A/C. Still, a customer may refill the water heatsink manually.

However, at least one of the heatsinks should preferably remain active to cool the air compressor head in any mode, and thus to maintain the air compressor in its workable condition.

Further, a brief description of the proposed method will be provided, which will also explain how the proposed system works.

The air is sucked from the premises into the compressor's head, and then compressed by the air compressor up to the denaturing pressure (for example of about 8-10 atm).

The pressure may be selected by the manufacturer and/or controlled by a customer, for example for selecting regimes related to different noxious organisms.

The compressed air is introduced into the pressure tank, for example via a non-return (one way) valve.

The compressed air is maintained in the pressure tank approximately at the same pressure, while heating the compressed air up to the denaturing temperature in the approximate range (170-250)° C.

The process is performed by dynamically maintaining the necessary denaturing pressure and temperature in the tank. If the organism/item of interest is maintained in the tank at the necessary conditions for about 3-12 seconds, this time period is considered by the Inventor as sufficient for denaturing the organism/item.

The process is terminated with discharging the sanitized air to the premises; it should be kept in mind that expansion of the compressed air will cause cooling of the air.

The air discharge may be performed continuously or periodically via a controllable valve connected to an air diffuser.

The compressed and heated air (which is thus sanitized) may be periodically discharged from the tank to the premises, upon maintaining each air portion in the tank for 3-12 seconds.

The whole process may be performed periodically, beginning from the suction step.

However, the whole process including the discharge may be performed continuously.

In such a case, different items of interest may be treated in the tank for different periods of time so that some of them may remain alive when discharged. Still, the air in the room will be recycled multiple times and thus will be gradually sanitized by the device.

Some additional details and features of the proposed air sanitizing system will be disclosed below.

Preferably, the system may be adapted for the controllable heating of the air in the pressure tank, based on a selected denaturing temperature depending on the type of organisms to be denatured.

To this end, the system may be provided with a control circuit comprising a control unit and at least a first temperature sensor of air temperature in the pressure tank, for controllably heating the compressed air in the pressure tank.

The control circuit may comprise more sensors of temperature and/or pressure (for example, a sensor of the room temperature, a pressure sensor).

The proposed system may additionally be provided with a filthiness sensor to detect air filthiness. The filthiness sensor may be connected to the control unit.

The control unit may be thus adapted for obtaining readings from said at least one sensor and issuing control commands to said compressor and said tank (more specifically, to the non-return valve, to the controllable valve, to the heating element/s, etc.).

In other words, the control circuit may be adapted to control/regulate the air flow through the pressure tank.

The pressure and the temperature in the pressure tank may be maintained dynamically. Indeed, the compressed air in the tank, heated up to a temperature within the denaturation temperature range, may build up an additional pressure in the tank.

On the other hand, the pressure and the temperature in the tank will decrease when the compressed air is controllably discharged from the tank. That dynamic balance may be maintained by a control circuit.

It should be kept in mind that the air obtained from the compressor (more specifically, from the compression head), reaches temperatures of about (150-180)° C. due to compression. Additional temperature rise may be obtained by heating the air in the pressure tank.

To this end, the pressure tank may be heated directly, and/or be equipped with one or more heating elements. In any case the pressure tank may be adapted to controllably keep the air inside the tank at a selected working temperature from the mentioned denaturation temperature range of about (170-250)° C., being close to a specific denaturation temperature suitable for a specific type of the small organisms/elements of interest.

For example, specific working temperatures may be found within an approximate working temperature range of about 200-220° C.

The pressure tank may be provided with heat insulation, to prevent heat dissipation there-from.

For example, a heating blanket may have at least two layers and may serve both as a heating element and as a heat insulation of the tank. In another example, the heating element(s) may be positioned inside the pressure tank.

The sanitized compressed air is then released from the pressure tank to a room pressure (1 atm), thus causing cooling of the released air due to expansion. It has been shown by the Inventor that the sanitized air expanded from the system, may have temperature of about 25° (C).

The system may be further provided with sound reducing means. While the system is supposed to be ON quite often (for example, and in particular at night), the problem of noise becomes extremely actual.

The noise reducing means may comprise one or more from the following non-exhaustive list: a noise reducing case enveloping the air compressor, at least one air silencer intended for reducing noise when discharging the compressed sanitized air.

The air compressor of the system may be provided with a sound reducing box (envelope). Its main function is blocking the sound waves by creating a barrier between the air inside and outside the box, while ensuring that heat is transferred away from the compressor to the heat sinks (for example, via heat tubes). The box may be empty or may comprise any filling material like fabric or fibers.

Other elements of the system may also be provided with sound reducing means.

For example the purified air, outgoing from the system, may be silenced by one or more of the following: 1) a flow regulator introduced into an egress line/pipe, 2) an air silencer connected in parallel to the egress line, 3) an air silencer connected in series/combined with the flow regulator. The air silencer may be implemented as an exhaust silencer, for example may comprise just a plastic body with a sintered polyethylene membrane.

As mentioned, for heating the compressed air in the pressure tank, the tank may be heated directly (i.e., may constitute a heating element) and/or may be provided with one or more internal heating elements. It goes without saying that the heating element should be energized from some power source.

The heating element may have various implementations. For example, it may form part of a heating blanket enveloping the pressure tank. The blanket may comprise an outer, heat insulating layer.

An internal heating element may be inserted (at least partially) inside the pressure tank. In one embodiment, the internal heating element may comprise one or more pin-like members installed in the pressure tank (for example, radially or axially). The pin-like members may be made of metal and be connected to electric power. Any internal heating elements should be hermetically fixed within the pressure tank.

As mentioned above, the inventive air sanitizing system may be manufactured in the form of a stand-alone device, preferably portable.

Alternatively, the proposed system (as a so-called integrated device) may be combined/integrated with an air conditioning (A/C) system of the premises.

In particular, the inventive system may use the A/C indoor unit, as will be further described below in the detailed description of the invention.

In any modification of the device, the device may be positioned/adapted to discharge the sanitized air to the output air stream of the AC, so that the discharged air be carried to the room together with the air stream of the AC, in a combined (mixed) air stream.

Preferably, the outlet of a duct bringing the sanitized or the combined air stream to a room should be positioned as far as possible from the inlet of a duct sucking air back from the room, so as to prevent the sanitized air from being immediately sucked again into the compressor of the sanitizing device, or into an internal A/C unit.

The combination of the inventive air sanitizing system and an air conditioning (A/C) system creates a novel modified system. Such a system is intended for gradually sanitizing the air which is circulated in the premises by the air conditioner.

Known modifications of an A/C system include a room A/C unit (for example, an indoor/internal unit of a room air conditioner), a central A/C system, a semi-central A/C system etc.

In the modified/combined system comprising an indoor A/C unit for a room, one air sanitizing system may be used; it may be installed to receive an air flow from the room and to output a purified (sanitized) air flow to the room, together with the air conditioned by the air conditioner unit.

Even in one room, for example when the room is large, the modified air conditioner in the form of a room A/C unit may optionally collect air from more than one different collecting locations and may then return the sanitized/conditioned air to more than one discharge locations in that room.

It should be kept in mind that the collecting locations are to be maximally spaced from the discharge locations.

The modified system may similarly serve a number of different rooms.

Actually, the modified air conditioner (A/C) system configured for premises, may comprise more than one air inlets for collecting air from different collecting locations in the premises for treatment in said internal unit, and may further comprise more than one outlets for returning, from said internal unit to different air discharge locations in the premises, conditioned air mixed with sanitized air.

When the modified system is based on a central or a semi-central A/C system, the proposed air sanitizing system (device) is combined with a common internal unit of the A/C system.

The functionality of such a configuration is:
to collect air from one or more rooms in a premises (for example, into an air collector),
to pass one portion of the air collected from said rooms, through the air sanitizing device, thus obtaining a sanitized air flow,
to pass another portion of the air, collected from said rooms, via the internal unit of the A/C system, thus obtaining a conditioned air flow,
to mix the sanitized air flow with the conditioned air flow in a common egress line (for example, in an air distributor) of the A/C system, thereby obtaining a mixed air flow, and then to spread the mixed air flow back to the rooms, for further circulation.

The proposed device may comprise a control panel. In the embodiment of the integrated device combined with the A/C, the control panel may form part of the A/C control panel.

The proposed device (system) may be fed with electricity from the air conditioner A/C, or directly from the line.

According to an additional aspect of the invention, there is also proposed an air conditioner (A/C) accommodating, in its internal unit, the above-described device for sanitizing air in a premises.

BRIEF DESCRIPTION OF THE DRAWINGS

The invention will be further described in more details with reference to the following non-limiting drawings in which.

DETAILED DESCRIPTION OF SPECIFIC EMBODIMENTS

Figure 1:
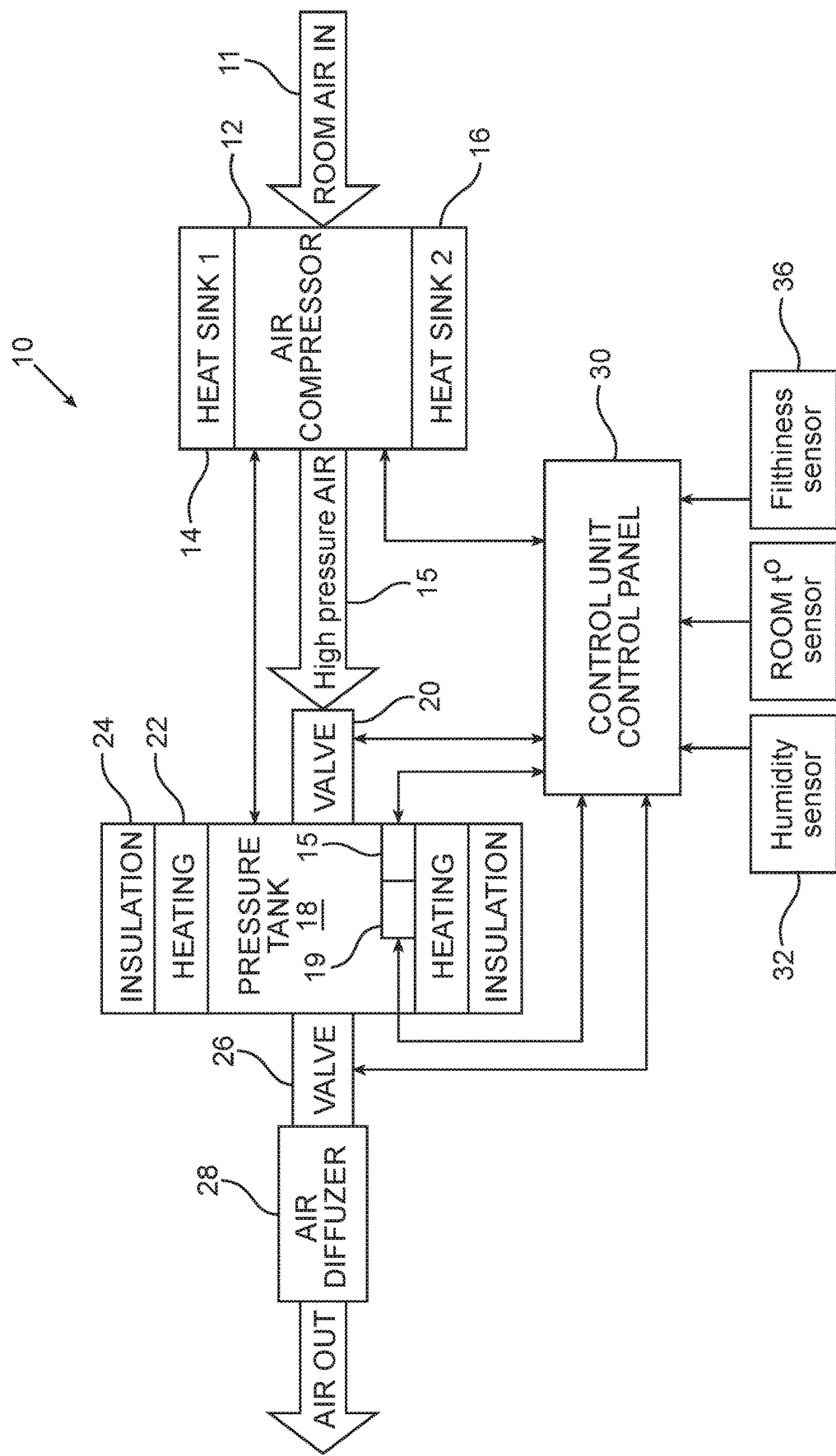
FIG. 1 illustrates an exemplary block-diagram illustrating the proposed concept.

FIG. 1 illustrates one schematic block diagram of the proposed denaturation system 10.

Air from the room to be sanitized is sucked into an air compressor (compressor head) 12 via inlet marked 11. The air compressor 12 may be cooled via two heatsinks 14 and 16.

Volumetric flow rate of the compressor head may be, for example, 50-100 or even up to 200 liter per minute, which is considered high for the proposed denaturation device. The air sucked in by the compressor head may be compressed up to 8-10 atm which is called the denaturation pressure range. The temperature of the air raises due to compression; in addition, the air may further heated in the pressure tank. While being useful for further denaturing of small organisms in the pressure tank, the mentioned air pressure afterwards allows sufficiently cooling the air during its expansion, when the air is discharged from the tank to the premises.

Meanwhile, the compressed air is fed (see arrow 15) to the pressure tank 18 via a non-return valve 20. In the tank, the air is additionally heated up to the sanitizing (denaturing) temperature (170-250)° C. so as to kill/denature the small organisms if present in the air.

The pressure tank 18 may be heated using a heating element 22 and an insulation layer 24, which both may be parts of a heating & insulation blanket.

For denaturing/killing of an organism such as a mite and for denaturing its associated allergens, the mite may be kept in the air pressure tank at the denaturation temperature during of about 3 to 12 seconds. It should be noted that due to the dynamic principle of the tank operation, some organisms sucked into the tank are kept there-inside quite enough time to be killed, but some of them make a faster transfer from the entrance to the exit. The continuous or periodic operation of the system ensures that the room air passes through the device multiple times and finally becomes fully sanitized (i.e., free from active small organisms/items/allergens).

The proposed system 10 takes air from the room and discharges it back to the room.

The air is discharged from the tank 18 via a controllable valve 26 to a diffuser 28, which gradually returns it to the room. The expanded air will be cooled to the temperature which does not cause excessive heating of the room (to of about 25° C.). The system may be controlled by a control unit and be provided with a control panel (block 30). The control unit 30 controls the system based on a selected denaturation temperature, readings of temperature sensor 19 of the tank 18, pressure sensor 15 of the tank 18, by using status of valves 20 and 26, and using readings of some other sensors 32, 34 (humidity and room temperature). In a simple version of the method, pressure sensor 15 checks the pressure inside the pressure tank to signal the compressor to stop or start working.

The proposed system 10 may additionally be provided with a filthiness sensor 36 to detect air filthiness. The filthiness sensor may be coupled with the control unit 30 which may be adapted to controllably adjust operation of the system according to the filthiness sensor's readings. Readings of the filthiness sensor may be used for indirectly checking the sterility assurance level SAL.

Control panel of the unit 30 may comprise buttons for selecting denaturation temperature, night mode, indication bulb of air quality, indication bulb that water should be filled (if the heatsink 16 is a water heatsink), etc.

The Inventor checked quality of air in exemplary premises before and after the proposed sanitizing, and came to the conclusion that the proposed technique achieves full sanitizing of the air, i.e. it is much more effective than known technologies.

The present invention improves efficiency of the small organisms' denaturation and improves overall quality of the technique owing to: introducing a pressure tank, using high temperature and high pressure in the pressure tank. The results are positively affected also by using greater CFM than in other denaturation devices, due to greater air exchanging efficiency and lesser heating of the room, and due to location of air discharge as far as possible from the air inlet.

All this is achieved with a relatively small volume of the proposed system which may be a stand-alone portable device or may form part of an A/C system in the premises. Examples of various implementations will be shown in FIGS. 2-4.

Figure 2:
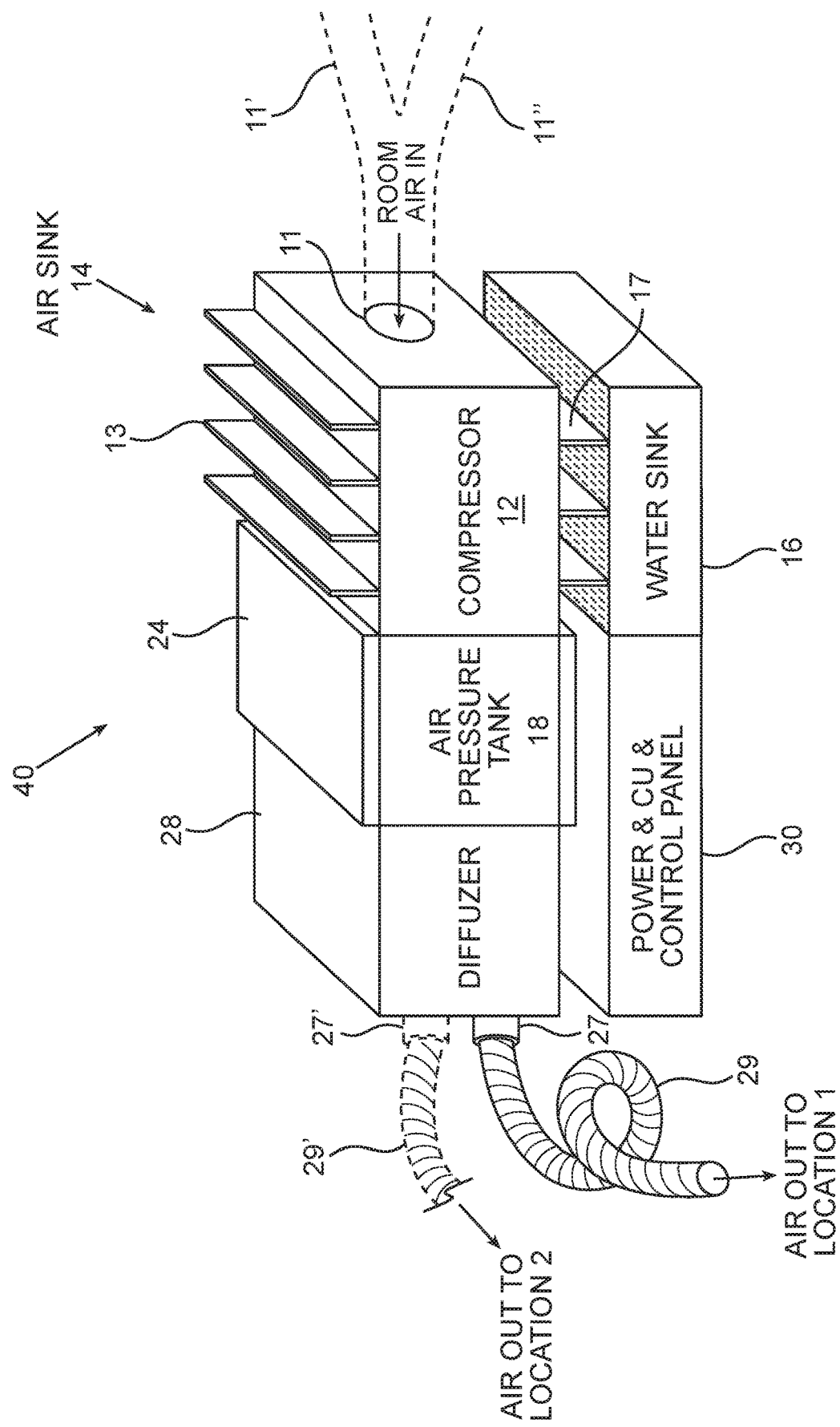
FIG. 2 illustrates one schematic exemplary embodiment of the proposed air sanitizing system which is a stand-alone device.

FIG. 2 is a schematic example of a stand-alone device 40 for sanitizing air in a premises, for example in one room. The device 40 comprises the same units as in FIG. 1. Those which are shown in this figure, are marked with similar numbers. In FIG. 2 the units are implemented as follows.

The air inlet 11 may optionally be fed from more than one ducts (11', 11", marked by dash lines) bringing air from different collecting locations in the premises to the compressor 12.

In this drawing, the first heat sink 14 is an air heat sink: the compressor head 12 is provided, for example, with radiator ridges 13. The ridges/cooling fins 13 may be cooled by the ambient air. An external, protective housing covering the ridges 13 may be made of a net/mesh (not shown).

The second, lower heatsink 16 is a water sink comprising ridges 17 immersed in the water filled in a pan provided under the device. The pan should be filled by a customer. The outlet 27 of the diffuser 28 may be provided with a hose 29 in order to discharge the sanitized air as far as possible from the air inlet 11 (Room air IN) of the Compressor 12. The hose 29 may be placed so that the output opening thereof is positioned close to a ventilator or to an outlet of an air conditioner, in order to mix the sanitized air from the hose 29 with the main air flow serving the room.

An additional outlet 27' with an additional hose 29' (shown in dashed lines) may be provided to supply the sanitized air to another discharge location in the premises (for example, an additional discharge location in a room with poor air circulation, or in another room).

Block 30 of device 40 accommodates its autonomous control unit and control panel.

The proposed air sanitizing system may form part of a combined system which also comprises any version of air-conditioner (A/C).

In a combined system comprising a room A/C unit, one air sanitizing system may be used. The air sanitizing system may be installed to receive a polluted air flow from the room and to output a purified/sanitized air flow to the room, together with the air conditioned by the air conditioner unit. Such options will be shown, for example, in FIGS. 3, 4.

Figure 3:
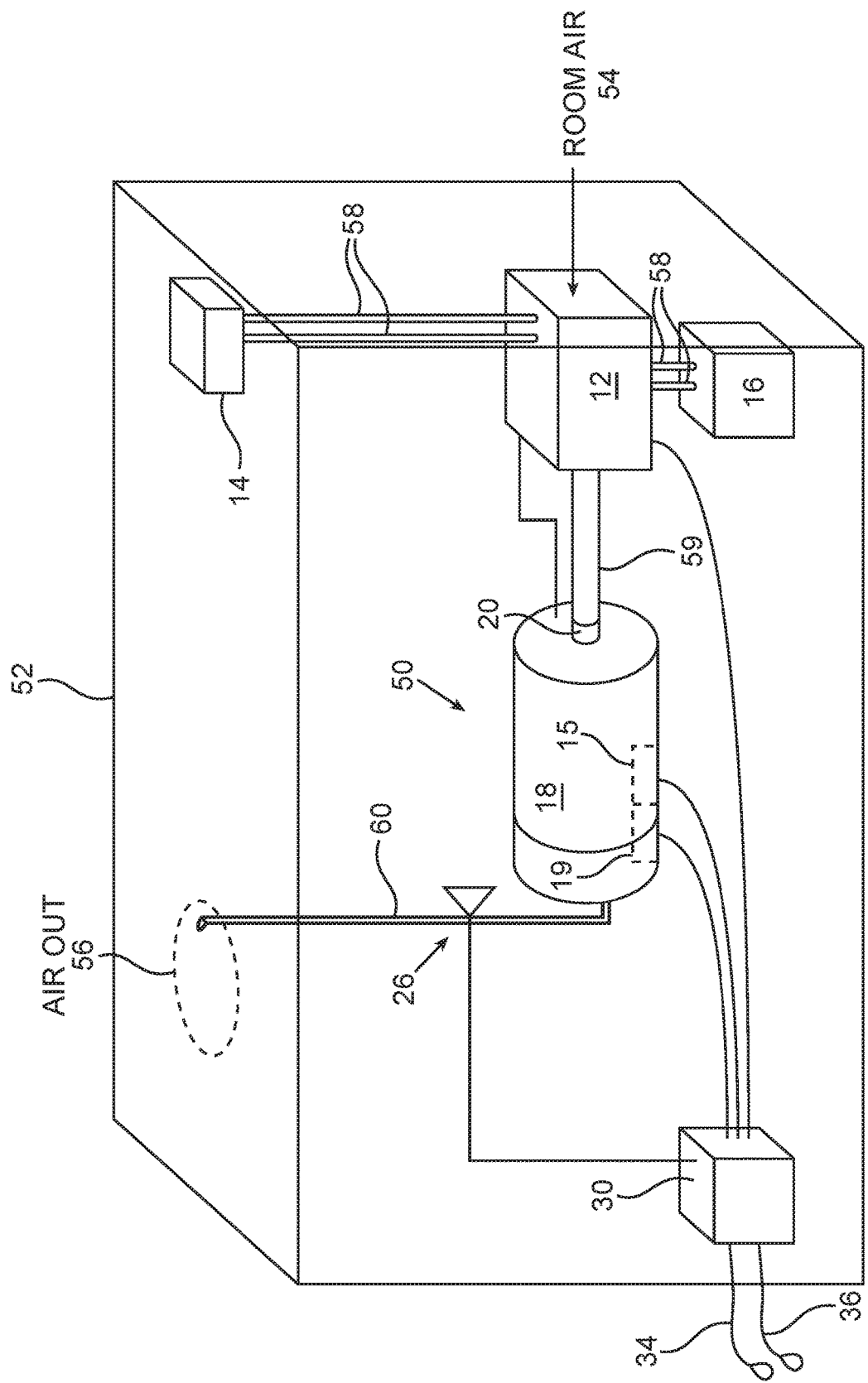
FIG. 3 is another schematic exemplary embodiment of the proposed air sanitizing system; in this embodiment, the system forms part of the inner unit of an A/C and is accommodated in the unit's housing.

FIG. 3 illustrates one possible embodiment 50 of the device integrated in an internal unit of an air conditioner (A/C), schematically shown as 52. Inlet for air to be cooled/heated by the air conditioner 52 is not shown. Inlet for room air is marked with arrow 54. Outlet 56 is for the sanitized air discharged and mixed with the cooled/heated air produced by the A/C 52. Air pipes are shown as 59 and 60. A controllable valve 26 may be used for regulating air flow through the outlet pipe 60, in order to reduce noise of the egressing air.

In any case, and especially in case the proposed system forms part of the A/C, the air discharged from the pressure tank 18 should be output in the direction of air coming out from the air conditioner (so it will be carried as far from the inlet as possible). In this figure, the discharged air is output via outlet 56 which is quite far from the inlet 54.

The A/C indoor unit, if used, may allow faster replacement of air in the room, since the faster the air is blown away from the outlet, the farther it gets so it will not be immediately sucked again into the described air sanitizing system.

In FIG. 3, the integrated denaturation device 50 comprises two heatsinks 14 and 16.

The device may use the AC heatsinks, but may have its separate heatsinks which are illustrated in FIG. 3.

The heatsink 14 comprises a heat conductive element/radiator cooled by air produced by the A/C. The radiator may be connected with the compressor 12 via heat pipes/heat connectors 58.

The heatsink 16 comprises a water container which is filled with water by condensate produced by the fan coil of A/C. The heatsink 16 also comprises a heat conductive element/radiator (for example, a saw-like, toothed or ribbed metal plate) at least partially submerged in the water container. In this drawings, the radiator is connected with the compressor 12 via heat pipes (heat connections) also marked 58.

Water in the heat sink container 16 will be heated until it is evaporated (or drained). The container may be continuously refilled by the A/C condensate. By computing the water rate of a specific AC, a specialist may estimate how much water will accumulate in the water container.

Both heatsinks 14 and 16 are designed to reduce the heat of the compressor head 12.

In case AC 52 works in a cooling mode, condensate will be condensed in the water container and cool the heatsink 16.

In case the AC 52 works in its heating mode, there will be no condensate and the heatsink 14 will be cooled by the hot air from the AC (and still cooled from about 180 to 30° C. Both heatsinks 14, 16 are connected to the compressor head 12, so they (and the head 12) maintain a similar temperature.

Figure 4:
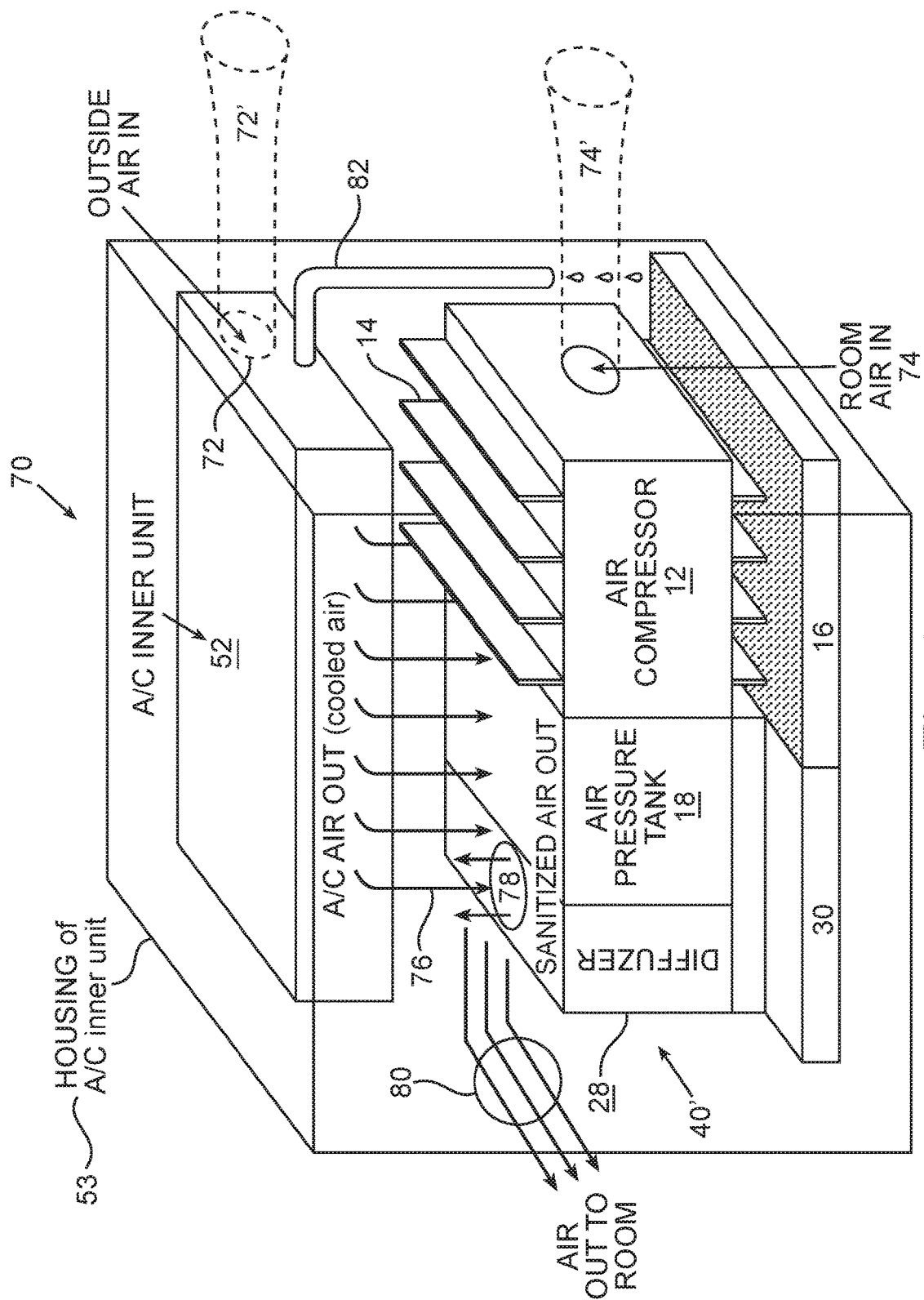
FIG. 4 is yet another schematic embodiment of the combined air sanitizing and air conditioning system.

FIG. 4 illustrates one additional exemplary implementation 70, where a device 40' (quite similar to the configuration shown in FIG. 2) is accommodated in a common modified housing 53 of the internal unit 52 of the air conditioner A/C. Inlet of outside air to the unit 52 (from an external unit of the A/C) is marked 72. Its optional duct is marked 72'.

Inlet 74 is for the room air to be sucked into the compressor 12. An optional inlet air duct is shown as 74'.

Outlet 78 is for the sanitized air discharged from the device 40'.

Outlet 80 is for outputting to the premises the resulting air flow produced by the unit 52 and the device 40'.

Let the A/C is in its cooling mode.

The flow of the cooled air produced by the unit 52 is indicated by arrows 76.

The sanitized air is discharged from the pressure tank 18 via the diffuser 28 and the outlet 78. The discharged air may have temperature of about 25° C. due to the pressure drop from of about 10 atm to of about 1 atm.

The cooled air flow 76 produced by the inner A/C unit 52 performs two functions: a) it cools the radiator of the heatsink 14 and b) it is simultaneously mixed with the sanitized air while discharged from the outlet 78. The mixed air is output to the room via the outlet 80 in the housing 53. The outlet 80 is shown schematically in the drawing. In practice it may have a standard rectangular shape and be provided with a conventional shutter. The water sink 16 may be filled with condensate from the unit 52, via a pipe 82.

Let the A/C is in its heating mode or in its air ventilation mode.

In this case, the airflow 76 of the A/C unit 52 will still be able to successfully perform cooling of the heat sink radiator 14. The air stream produced by the system 70 and outputted from the outlet 80 will comprise: the sanitized air discharged from the device 40' at a temperature of about 25° C. and the air 76 produced by the A/C in its heating or ventilation mode.

The water pan of the heatsink 16 may be refilled by water by a customer (a suitable opening may be provided, though not shown in the drawing). In case the housing 53 is configured so that air flow 76 reaches the radiator of heatsink 16, the heatsink 16 may also be air cooled.

The proposed system 70 may comprise the A/C control panel, which incorporates the control panel of the device 40' (marked 30 in the drawing).

Figure 5:
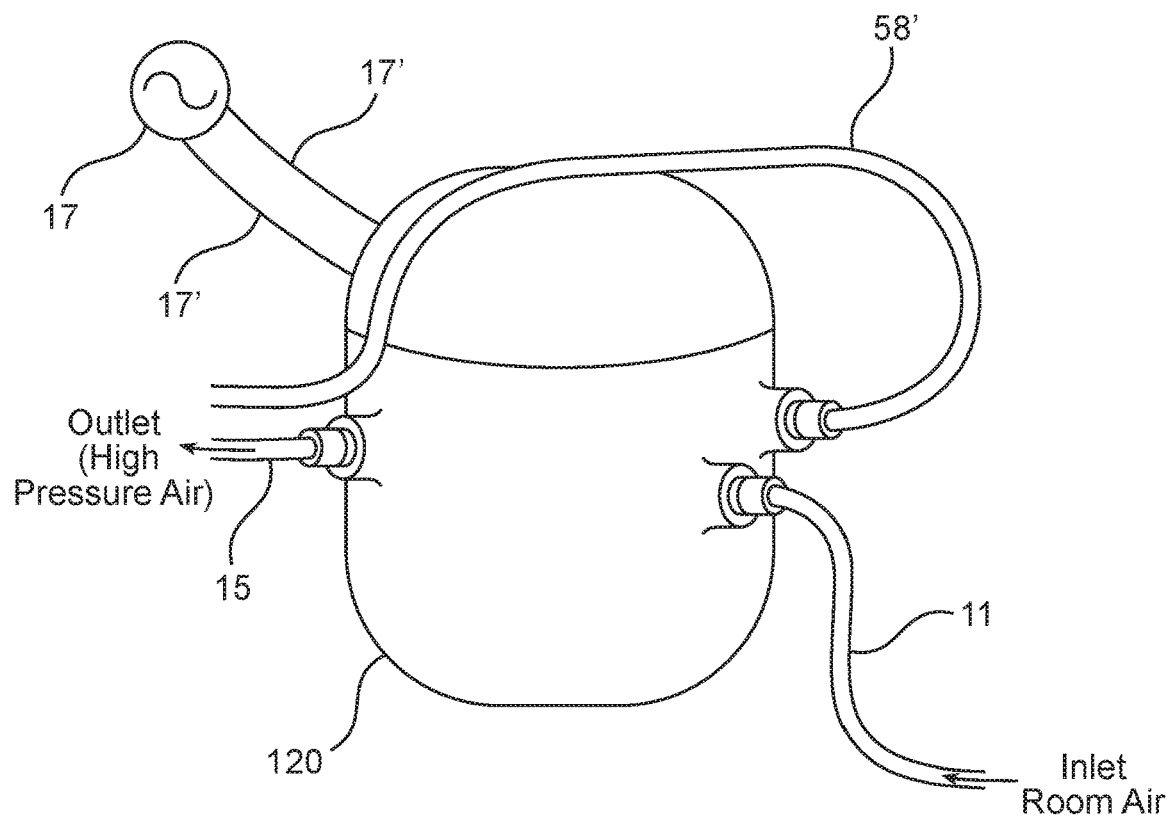
FIG. 5 depicts one embodiment of a compressor for the proposed air sanitizing system, which is provided with sound reducing means.

FIG. 5 depicts one specific embodiment of a compressor 12 for the proposed air sanitizing system, which is provided with noise reducing means. The proposed air sanitizing system is supposed to be ON quite often, and sometimes during all the day/night, it should not disturb the customers by noise.

In FIG. 5, the air compressor of the system is provided with a sound reducing box (casing) 120. Air inlet from a room is indicated as 11, while outlet of the high pressure air is marked by 15. The casing 120 may be made of metal and may serve as a heat sink. Its second function is blocking the sound waves by creating a barrier between the air inside and outside the casing, while ensuring that heat is transferred away from the compressor to another heat sink (for example, via heat tube 58'). The casing 120 may be empty (i.e., shaped just as a shell) or may comprise any filling material like fabric or fibers.

Figure 6:
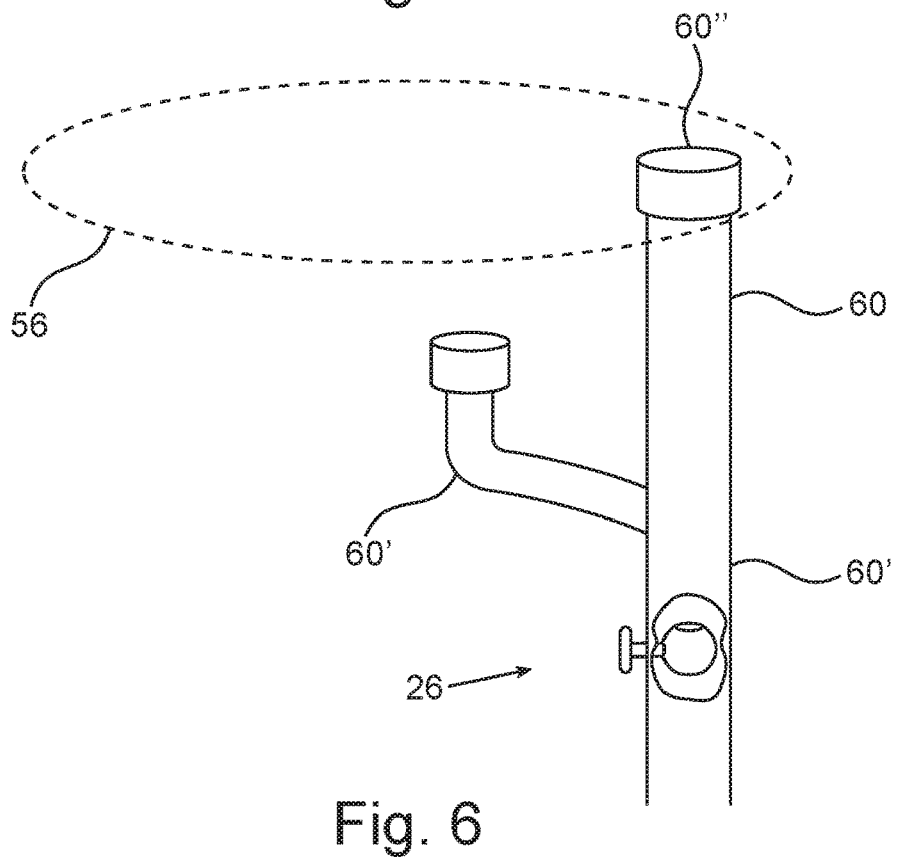
FIG. 6 schematically illustrates one embodiment of sound reducing means for an egress duct of the air sanitizing device.

FIG. 6 schematically illustrates another embodiment of sound reducing means for an egress line of the air sanitizing device. FIG. 6 is an enlarged portion showing the outlet portion of line 60 in FIG. 3, positioned in proximity to the outlet opening 56 of the air conditioner.

The compressed purified air, egressing from the air sanitizing system, may be silenced by one or more of the following: 1) a flow regulator 26 introduced into an egress line/pipe 60, 2) an air silencer 60' connected in parallel to the egress line, 3) an air silencer 60" connected in series or combined with the flow regulator 26. The air silencer may be implemented as an exhaust silencer, for example may comprise just a plastic body with a sintered polyethylene membrane.

Figure 7:
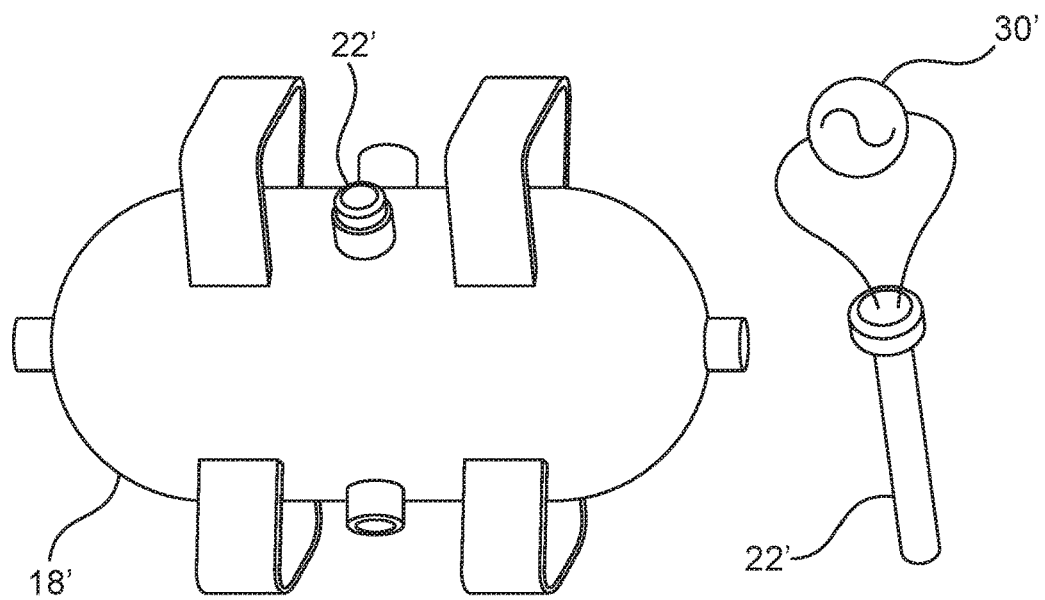
FIG. 7 schematically illustrates one embodiment of the pressure tank provided with heating elements.

FIG. 7 schematically illustrates an exemplary embodiment 18' of the pressure tank provided with heating elements (members) 22'. As mentioned, the pressure tank of the air sanitizing system may be heated in various ways. It may be heated directly (i.e., may itself be a heating element) and/or may be provided with one or more separate heating elements. In any option, the heating element(s) will be energized from a suitable power source.

In one example (which is not illustrated here), the heating element forms part of an outer blanket enveloping the pressure tank. The blanket may comprise the heating element as an inner layer intended to be placed in close proximity to the tank, and an outer, heat insulating layer which covers the inner heating layer.

FIG. 7 illustrates a specific embodiment of an internal heating element installed in the pressure tank; in this example, the internal heating element comprises two heating members (marked as 22') installed in the pressure tank radially and fixed hermetically within the pressure tank. The heating members 22' may be made of metal and be connected to an electric power source 30'. Pin-like members 22' may be axially shifted from one another when installed in the tank 18'. Alternatively, heating members 22' may have shapes differing from the pin-like shape shown in FIG. 7 near the tank 18', and thus may be installed in the tank as shown in the figure. Yet another option is that only one heating element 22' is installed, while additional orifices in the pressure tank may be equipped with means (not shown) for drainage of the tank.

As mentioned above, the proposed air sanitizing system may form part of a central or a semi-central A/C system, and be combined therein with a common internal unit of the A/C system.

The function of such a modified A/C system will be:
to collect air from one or more rooms in a premises (for example, into an air collector),
to pass one portion of the air collected from said rooms, through the air sanitizing device, thus obtaining a sanitized air flow,
to pass another portion of the air, collected from said rooms, via the internal unit of the A/C system, thus obtaining a conditioned air flow,
to mix the sanitized air flow with the conditioned air flow in a common egress line (for example, in an air distributor) of the A/C system, thereby obtaining a mixed partially sanitized air flow, and then
to spread the mixed (partially sanitized and conditioned) air flow back to the rooms.

Figure 8:
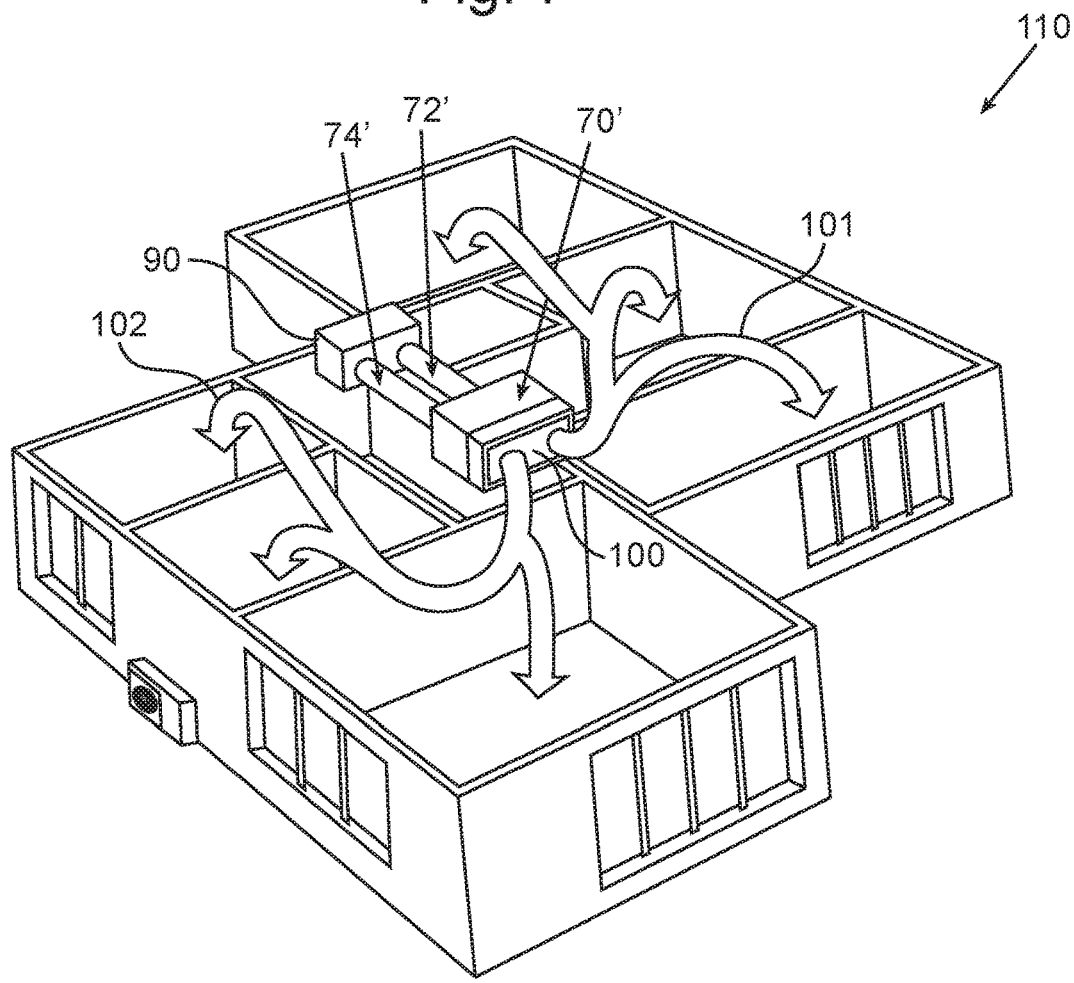
FIG. 8 is a schematic plan view of a house with an exemplary central air conditioning (A/C) system, combined with the proposed air sanitizing system.
Figure 9:
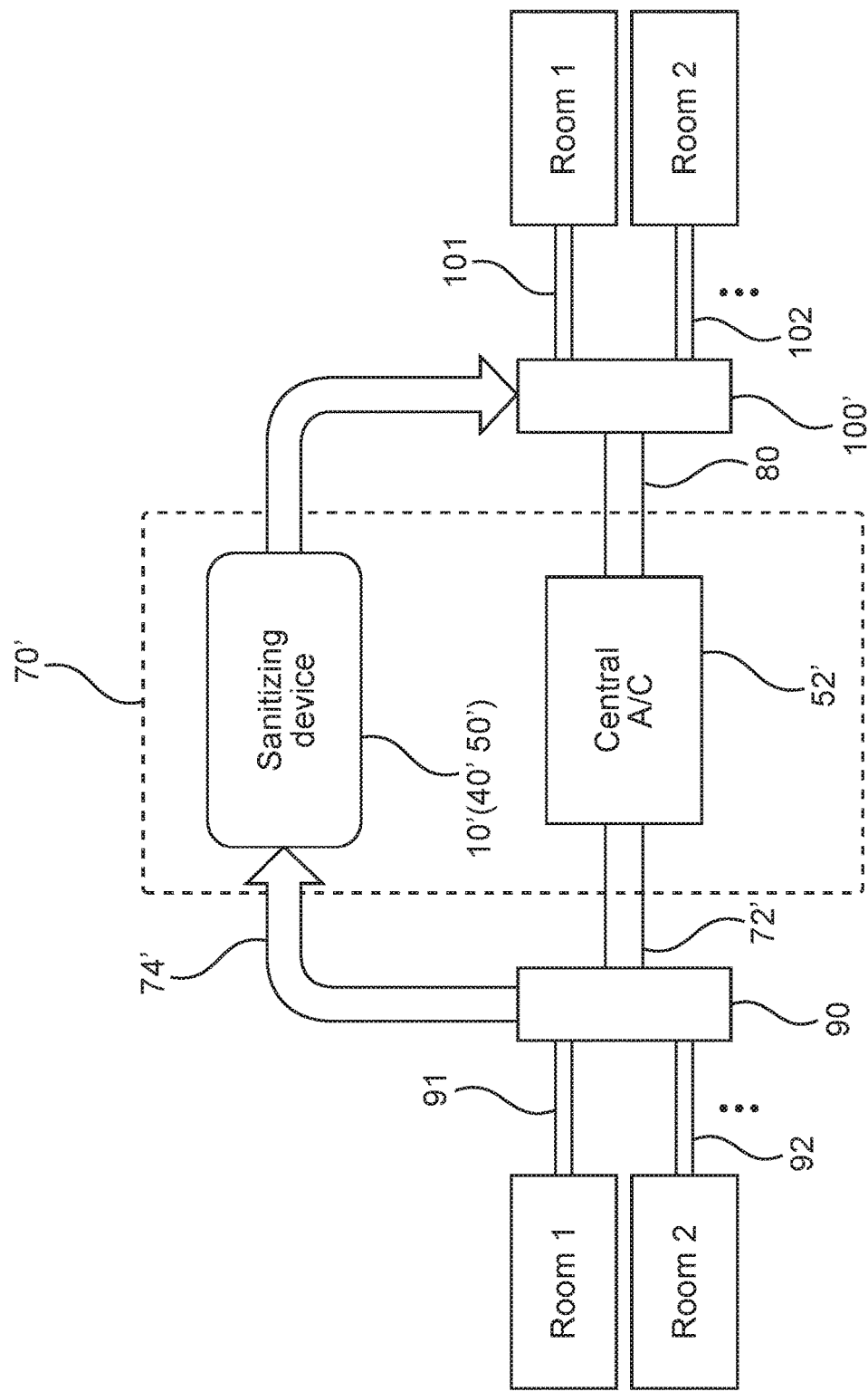
FIG. 9 is a schematic block diagram illustrating operation of the combined central air conditioning (A/C) and air sanitizing system shown in FIG. 8.

FIGS. 8 and 9 schematically show such a modified central A/C system 110 in a house having at least two rooms. System 110 provides sanitizing and conditioning of the air circulating in the premises.

FIG. 8 is a schematic plan view of a house with an exemplary central air conditioning (A/C) system, combined with the proposed air sanitizing system, while FIG. 9 is a schematic block diagram illustrating operation of the combined central air conditioning (A/C) and air sanitizing system shown in FIG. 8.

An air sanitizing system and an internal central A/C unit are combined into a central modified block indicated 70' (which may be similar to block 70 of FIG. 4). In FIG. 9, the air sanitizing system is marked as 10' (40', 50') since it may be configured similarly to systems 10, 40, 50 respectively shown in FIGS. 1, 2, 3.

In FIGS. 8 and 9, two ingress lines 72', 74' of the central modified block 70' are connected to an air collector 90, while a common egress line of block 70' is connected to an air distributer 100. The air collector 90 and the air distributor 100 are parts of the conventional central A/C system.

The air collector 90 collects air from rooms of the premises. Ingress ducts leading air from the rooms are not shown in FIG. 8, but shown in FIG. 9 as exemplary ducts 91, 92.

As mentioned, the air collector 90 is connected to the central modified block 70' via the two ingress lines 72' and 74', which supply one part of the room air to the air sanitizing system (marked as 10', 40', 50' in FIG. 9), and another part of the room air—to the A/C central unit (shown as 52' in FIG. 9). The sanitized air from the sanitizing system 10' is mixed with the conditioned air from the A/C unit 52' in the common egress line 80 which terminates with air distributor 100.

From the distributor 100, egress ducts (101, 102 and the like) of the modified A/C unit 70' conduct the mixed, partially sanitized and partially conditioned air to corresponding rooms. After a number of repeating cycles, the air in the rooms becomes completely sanitized.

The air egress ducts 101, 102 and the like may be arranged to pass through walls/ceilings of the rooms.

While the invention has been described with reference to a number of specific implementation and versions of the method, it should be appreciated that other embodiments and versions may be proposed and should be considered part of the invention whenever defined by the claims which follow.

The invention claimed is:

1. A system for sanitizing air in a premises, comprising:
an air compressor for sucking air comprising noxious and/or allergenic small items, and compressing the sucked air up to a denaturing pressure,
a controllable pressure tank for denaturing there-inside said noxious and/or allergenic small items, said tank being adapted for controllably
introducing the compressed air from the compressor to the tank
heating the compressed air in the tank and maintaining the compressed air within a denaturing temperature range,
discharging the compressed sanitized air to the premises, wherein the discharged air cools down while expanding.

2. The system according to claim 1, comprising controllable valves for introducing the compressed air into the pressure tank, and for discharging air from the pressure tank.

3. The system according to claim 1, comprising a first and/or a second heatsink(s) to cool the air compressor.

4. The system according to claim 1, configured as a stand-alone device.

5. The system according to claim 1, adapted for being integrated in an internal unit of an air conditioner.

6. The system according to claim 5, wherein a first heatsink comprises a first radiator configured to be positioned in a flow of outgoing air produced by the air conditioner.

7. The system according to claim 1, wherein a second heatsink is a water heatsink configured for cooling the air compressor by water.

8. The system according to claim 7, wherein a second water sink comprises a water reservoir refillable by condensate produced by an air conditioner.

9. The system according to claim 1, provided with a control circuit comprising a control unit and at least a first temperature sensor of air temperature in the pressure tank, for controllably heating the compressed air in the pressure tank.

10. The system according to any claim 1 wherein the pressure tank is equipped with one or more heating elements adapted to controllably keep the air inside the tank at a selected working temperature.

11. The system according to claim 10, wherein said one or more heating elements comprise at least one member of the group consisting of the pressure tank itself, an inner layer of a heating and insulating blanket covering the pressure tank, and internal heating members installed in the pressure tank.

12. An air conditioner (A/C) accommodating, in its internal unit, a system according to claim 1 for sanitizing air in the premises.

13. The air conditioner (A/C) according to claim 12, adapted to discharge a combined air stream comprising sanitized air mixed with conditioned air.

14. The air conditioner (A/C) according to claim 12, comprising more than one air inlets for collecting air from different collecting locations in the premises for treatment in said internal unit, and further comprising more than one outlets for returning, from said internal unit to different air discharge locations in the premises, sanitized air mixed with conditioned air.

15. The system according to claim 1, adapted to operate periodically or continuously.

16. A method tor sanitizing air in a premises, comprising:
sucking air comprising noxious and/or allergenic small items into an air compressor and compressing the sucked air up to a denaturing pressure,
controllably
introducing the compressed air from the compressor to a pressure tank
heating the compressed air in the tank and maintaining the compressed air within a denaturing temperature range,
discharging the compressed sanitized air to the premises, so that the discharged air cools down while expanding.

17. The method according to claim 16, wherein the denaturing pressure is in an approximate range (8-10) atm, and the denaturing temperature is in an approximate range (170-250°) C.

18. The method according to claim 16, wherein the heated air is maintained in the tank during of about 3-12 seconds before discharging it.

19. The method according to claim 16, comprising selection of the denaturing temperature suitable for a type of organisms to be denatured.

20. The method according to any claim 16, performed periodically or continuously.

* * * * *